United States Patent [19]

Levin

[11] Patent Number: 5,763,675

[45] Date of Patent: Jun. 9, 1998

US005763675A

[54] PROCESS FOR THE PREPARATION OF 2-HYDROXYARYLALDEHYDES UNDER REDUCED PRESSURE

[75] Inventor: Daniel Levin, Manchester, United Kingdom

[73] Assignee: Zeneca Limited, London, England

[21] Appl. No.: 578,658

[22] PCT Filed: Jun. 6, 1994

[86] PCT No.: PCT/GB94/01227

§ 371 Date: Jan. 5, 1996

§ 102(e) Date: Jan. 5, 1996

[87] PCT Pub. No.: WO95/01951

PCT Pub. Date: Jan. 19, 1995

[30] Foreign Application Priority Data

Jul. 8, 1993 [GB] United Kingdom .................. 9314159

[51] Int. Cl.[6] .................................................... C07C 45/00
[52] U.S. Cl. ........................................................... 568/433
[58] Field of Search ........................... 568/716, 425, 568/426, 433

[56] References Cited

FOREIGN PATENT DOCUMENTS

| 529 870 | 3/1993 | European Pat. Off. |
| 583 910 | 2/1994 | European Pat. Off. |

*Primary Examiner*—Gary Geist
*Assistant Examiner*—Karl J. Puttlitz, Jr.
*Attorney, Agent, or Firm*—Pillsbury Madison & Sutro LLP

[57] ABSTRACT

A method for the preparation of a 2-hydroxyarylaldehyde which comprises reacting a magnesium bis-hydrocarbyloxide, derived at least in part from a hydroxyaromatic compound having at least one free position ortho to the hydroxyl group, with formaldehyde or a formaldehyde-liberating compound under substantially anhydrous conditions at a pressure of from 50 to 700 mm Hg absolute.

24 Claims, No Drawings

PROCESS FOR THE PREPARATION OF 2-HYDROXYARYLALDEHYDES UNDER REDUCED PRESSURE

This application claims benefit of international application PCT/GB94/01227, filed Jun. 6, 1994.

This invention relates to a chemical process and more particularly to a method for the preparation of 2-hydroxyarylaldehydes.

A number of 2-hydroxyarylaldehydes are known as useful products in the perfume and agricultural chemical industries and especially as intermediates for the corresponding oximes, for example 5-nonylsalicylaldoxime, which are used as metal extractants.

Our EP-A-0529870 describes a method of preparing 2-hydroxyarylaldehydes by reacting a magnesium bis-hydrocarbyloxide, derived at least in part from a hydroxyaromatic compound having at least one free position ortho to the hydroxyl group, with formaldehyde or a formaldehyde-liberating substance under substantially anhydrous conditions.

In particular, EP-A-0529870 describes reacting a magnesium bis-phenoxide, such as magnesium bis(4-nonylphenoxide), with paraformaldehyde in a substantially anhydrous solvent system at reflux temperature so that the volatile by-products of the reaction, for example methanol, methyl formate and methylal, are distilled from the reaction mixture as they are formed. It is stated that the reaction is preferably carried out at atmospheric pressure but that higher pressures may be employed if desired.

It has now been found that it can be advantageous to carry out the aforesaid formylation reaction at reduced pressures, that is to say at pressures lower than normal atmospheric pressure. In particular, it has been found that, in addition to facilitating removal of volatile reaction by-products, a significant improvement in the yield of and/or purity of aldehyde and an appreciable reduction in formation of by-products can be observed when the reaction is carried out at reduced pressure (and consequently at a lower temperature) compared with carrying out the same reaction in the same solvent system at atmospheric pressure.

Accordingly, the invention provides a method for the preparation of a 2-hydroxyarylaldehyde which comprises reacting a magnesium bis-hydrocarbyloxide, derived at least in part from a hydroxyaromatic compound having at least one free position ortho to the hydroxyl group, with formaldehyde or a formaldehyde-liberating compound under substantially anhydrous conditions at a pressure of from 50 to 700 mm Hg absolute.

The substantially anhydrous conditions required by the reaction may be conveniently provided by the use of substantially anhydrous reactants together with conventional techniques, for example distillation, for removal of adventitious moisture. It is usually advantageous to perform the reaction in the presence of a substantially anhydrous solvent system. Suitable solvent systems typically comprise an inert non-polar or low polarity organic solvent and/or a polar organic solvent capable of acting as a ligand with respect to magnesium atoms.

Suitable inert non-polar or low polarity organic solvents will be liquids at the reaction temperature and will act as solvents for the magnesium bis-hydrocarbyloxide. Preferably, they will allow removal of one or more of the volatile by-products by distillation during the course of the reaction. Examples of suitable inert solvents include aromatic hydrocarbons, for example toluene, xylene, mesitylene, cumene, cymene, tetralin and chlorinated aromatic hydrocarbons, for example chlorobenzene and o-dichlorobenzene. Mixtures of inert solvents may be used.

Suitable polar solvents will be liquids at the reaction temperature and may be regarded as co-solvents when used in conjunction with non-polar or low polarity solvents. As examples of suitable polar co-solvents, there may be mentioned polar aprotic solvents such as dimethylsulphoxide, sulpholane, dimethylacetamide, N-formylpiperidine, N-methylpyrrolidinone, tetramethylurea and, especially, dimethylformamide, tertiary bases such as triethylamine, tri-octylamine, tetramethylethylenediamine and pyridine, ethers such as diethyl ether, diphenyl ether, tetrahydrofuran, glyme, diglyme, triglyme, tris[2-(2-methoxyethoxy)ethyl] amine and crown ethers and other polar solvents such as "Polymeg" 1000 and "Cellosolve" and the like. Particularly useful co-solvents include lower alkanols such as ethanol and, especially, methanol. Mixtures of co-solvents may be used. The co-solvent may be incorporated into the reaction mixture as such or in the form of a ligand already complexed with the magnesium atoms of the bis-hydrocarbyloxide.

Some solvent materials may have the ability to function as both "solvent" and "co-solvent" in the method of the invention. Thus, for example, a material such as tetrahydrofuran may be used as a solvent in conjunction with a higher polarity co-solvent or as a co-solvent in conjunction with a lower polarity solvent or it may be used as the sole solvent/co-solvent.

Magnesium bis-hydrocarbyloxides which may be used in the method of the invention are compounds containing two hydrocarbyloxy residues per magnesium atom, at least one of said hydrocarbyloxy residues being aryloxy, for example phenoxy or naphthyloxy, having at least one free position ortho to the oxygen atom, especially phenoxy residues derived from phenols of Formula 1 and Formula 3 defined below. Especially suitable are magnesium bis-phenoxides wherein the phenoxide residues may be unsubstituted or may be substituted in any or all of the positions, other than both the 2- and 6-positions, by substituents which do not interfere with the course of the reaction and which preferably are electron-donating or weakly electron-withdrawing.

The invention is especially concerned with the use of magnesium bis-phenoxides derived from phenols of the formula:

(1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy or acyl group, for the preparation of 2-hydroxyarylaldehydes of the formula:

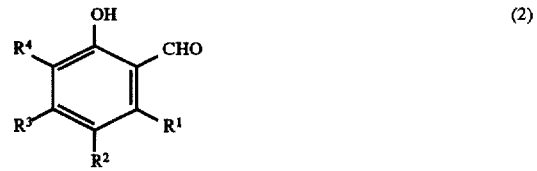

(2)

Each of the various hydrocarbyl, hydrocarbyloxy and acyl groups which may be represented by $R^1$, $R^2$, $R^3$ and $R^4$ suitably contains up to 36 carbon atoms, for example from 5 to 22 carbon atoms.

Particular mention may be made of magnesium bis-phenoxides derived from phenols of the formula:

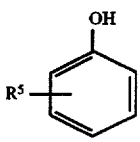

wherein $R^5$ represents hydrogen or a $C_{1-22}$-alkyl radical, said compounds being used in the preparation of 2-hydroxyarylaldehydes of the formula:

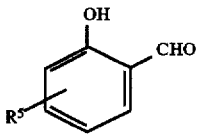

Preferably, $R^5$ is a $C_{7-12}$-alkyl radical, especially in the 4-position relative to the hydroxyl group.

The magnesium bis-phenoxides derived from phenols of Formula 1 or Formula 3 may be regarded as compositions containing structures of Formula 5 or Formula 6 respectively as well as related but more complex structures containing more than one magnesium atom per molecule.

In structures of Formula 5:

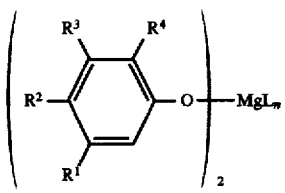

each of $R^1$, $R^2$, $R^3$ and R4 is as defined above, L represent a ligand molecule derived from another component of the reaction mixture and n represents an integer from 1 to 6.

In structures of Formula 6:

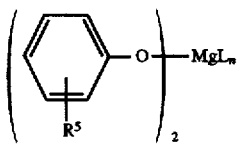

$R^5$, L and n are as defined above.

Components of the reaction mixture which may provide the ligand molecules L include the co-solvent, formaldehyde and the methanol by-product and mixtures thereof.

It is particularly convenient, however, to use a magnesium bis-aryloxide which, because of its method of preparation, already contains appropriate ligand molecules.

Thus, it is preferred to use a magnesium bis-hydrocarbyloxide which has been prepared by the method described by Ramirez et al in Synthesis, 1979, 71, that is to say by reacting a magnesium alkoxide of the formula:

$$Mg(OR^6)_2 \quad (7)$$

wherein R6 represents an alkyl, for example a $C_{1-4}$-alkyl, radical, especially methyl, with up to two moles of a phenol having at least one unsubstituted position adjacent to the phenolic hydroxyl group, for example a phenol of Formula 1 or Formula 3. Preferred ratios are from 0.9 to 2, especially from 1.5 to 2, typically about 1.66, moles of phenol per mole of magnesium alkoxide.

The magnesium bis-aryloxides, when used in the method of the invention, contain two aryloxy residues per magnesium atom and are believed also to contain one or more ligand molecules or groups, for example methanol molecules, such that they correspond or are structurally analogous to Formula 5. It is to be understood, however, that the present invention is not based upon any theory as to the precise structure of the magnesium bis-aryloxides and is to be regarded as relating to the use of said bis-aryloxides whether in the form of complexes of Formula 5 or not.

Other magnesium bis-hydrocarbyloxides which may be used in the method of the invention include compounds containing one aryloxy and one other hydrocarbyloxy, for example alkoxy, residue per magnesium atom. Such bis-hydrocarbyloxides may be obtained, for example, by reacting one mole of a magnesium alkoxide of Formula 7 with approximately one mole of a phenol having at least one unsubstituted position adjacent to the phenolic hydroxyl group and may, if desired, be used alone or in admixture with the aforementioned bis-aryloxides.

The formaldehyde used in the method of the invention may be in the form of free gaseous formaldehyde or a solution thereof in an anhydrous solvent or a formaldehyde-liberating compound, that is to say a compound capable of liberating formaldehyde under the conditions employed in the method of the invention. Suitable formaldehyde- liberating compounds include polymeric forms of formaldehyde such as paraformaldehyde. It is preferred to add the formaldehyde or formaldehyde-liberating compound gradually (continuously or discontinuously) to the bis-aryloxide in the solvent system.

The formaldehyde or formaldehyde-liberating compound is generally employed in the method of the invention in an amount of at least two moles, expressed as formaldehyde (HCHO), per mole of phenol present in the bis-hydrocarbyloxide. Preferred ratios are from 2 to 3, typically about 2.75 moles of formaldehyde per mole of phenol in the bis-hydrocarbyloxide. The co-solvent is suitably used in an amount not exceeding 5 moles per mole of bis-hydrocarbyloxide, preferred amounts being in the range from 1 to 2 moles per mole of bis-hydrocarbyloxide. These amounts include any co-solvent already present as ligand in the bis-hydrocarbyloxide. Since methanol is a by-product of the reaction, conversion and yield may be maximised by removing this methanol and any other volatile by-products by distillation during the course of the reaction so as to maintain the co-solvent/bishydrocarbyloxide ratio at the optimum level.

The optimum temperature for performing the reaction on which the method of the invention is based will depend to some extent on the structure of the particular magnesium bis-hydrocarbyloxide being used and also on the constitution of the solvent system and the pressure used to maintain distillation but can readily be determined by trial. In general, it is preferred to carry out the reaction at a reflux temperature in the range from about 70° to about 80° C., for example about 75° C., the reaction pressure being selected to maintain distillation. Pressures in the range from 50 to about 500 mmHg (absolute) will generally provide the preferred reflux temperatures.

At the end of the reaction, the 2-hydroxyarylaldehyde product may be isolated from the reaction mixture using conventional methods. Thus, the cooled reaction mixture may be drowned into cold dilute acid and the aqueous mixture may then be extracted with a suitable organic solvent such as toluene which may then be removed by distillation leaving the crude 2-hydroxyarylaldehyde which may be subjected to further conventional purification as desired.

The method of the invention is particularly suitable for use in the preparation of 5-alkylsalicylaldehydes of the formula:

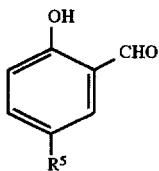
(8)

wherein $R^5$ is as defined above, from the corresponding magnesium bis- (4-alkylphenoxides). Thus, 4-nonylphenol (a mixture of isomers derived from phenol and propylene trimer) may be converted to the corresponding magnesium bis-phenoxide which may be used in the method of the invention to prepare 5-nonylsalicylaldehyde. Particularly suitable reaction conditions include the use of toluene or xylene as the inert solvent with methanol as the co-solvent at a reaction pressure of from 50 to about 400 mm Hg. The 5-nonylsalicylaldehyde is useful as an intermediate in the manufacture of the metal extractant 5-nonylsalicylaldoxime.

The invention is illustrated but not limited by the following Examples:

Example 1

Methanol (225 g) and toluene (108 g) were charged to a reaction vessel followed by particulate magnesium (2.92 g). An activator solution (10 g) was added to activate the magnesium and the mixture was heated to reflux temperature (65° C.) to achieve magnesium dissolution with evolution of hydrogen gas. The mixture was maintained at reflux temperature for 0.5 h and then further magnesium was added in four portions (4×2.92 g) over a total period of 1.5 h, each portion being added once hydrogen evolution from the previous portion had subsided. The mixture was then heated under reflux for a further 1.5h to ensure complete magnesium dissolution and 4-nonylphenol (224 g) was added. The activator solution was taken from a composition (1116 g) containing nonylphenol magnesium salt (461 g), magnesium methoxide (17.3 g), toluene (194 g) and methanol (443.7 g).

Toluene (208 g) was added and methanol-toluene azeotrope (303 g) was removed by distillation under reduced pressure (350–400 mm Hg) with fractionation, distillate being removed up to the point where the reaction mixture viscosity increased and the reaction temperature reached 75° C. at 380 mm Hg.

An agitated slurry of paraformaldehyde (92.8 g) in toluene (130 g) was added to the resulting toluene solution of the nonylphenol magnesium salt under reduced pressure at 75° C. over 2 h with removal of toluene and volatile by-product distillates. The reaction temperature was maintained at 75° C. throughout the addition by reducing the pressure from 380 to 260 mmHg. On completion of paraformaldehyde addition, heating was continued at 75° C. under reduced pressure (260 mm Hg) for 1 h to ensure completion of reaction and the mixture was then cooled to 30°–40° C.

The reaction mixture was drowned out into a mixture of cold water (750 g) and sulphuric acid (122.5 g), maintaining the temperature of the mixture between 30° C. and 40° C. The whole mixture was stirred at 30°–40° C. for 2 hours then allowed to settle and the upper (organic) layer was separated from the lower (aqueous) layer.

The organic layer was washed with water (2×250 g) until acid-free and toluene was then removed by distillation under reduced pressure at up to 90° C. to leave the crude 5-nonylsalicylaldehyde as a yellow oil (253 g, 83.3% strength, 85% yield from nonylphenol). The aldehyde was purified by distillation at 205°–210° C./20 mm Hg.

When the same reaction is performed in toluene at atmospheric pressure and a temperature of 95°–100° C., 5-nonylsalicylaldehyde is obtained in 78.8 yield (78.8% strength).

Example 2

Methanol (112.5 g) and particulate magnesium (1.825 g) were charged to a reaction vessel. An activator solution (2 g of 8% magnesium methoxide in methanol) was added to activate the magnesium and the mixture was heated to reflux temperature (64° C.) to achieve magnesium dissolution with evolution of hydrogen. The mixture was maintained at reflux temperature for 20 minutes and then further magnesium was added in three portions (3×1.825 g) over a total period of 1 hour, each portion being added once hydrogen evolution from the previous addition had subsided. The mixture was then heated at reflux for a further hour to ensure complete dissolution of magnesium and 4-nonylphenol (112.0 g) was added. The resulting solution was refluxed for 1 hour at 67° C.

Xylene (130.0 g) was added and a methanol-xylene azeotrope (95 g) was removed by distillation under reduced pressure (210 mm Hg) with fractionation, distillate being removed up to the point where the reaction mixture viscosity increased and the reaction temperature reached 75° C. at 210 mm Hg.

An agitated slurry of paraformaldehyde (45.0 g) in xylene (65.0 g) was added to the resulting xylene solution of the nonylphenol magnesium salt under reduced pressure over 2 hours. The reaction temperature was maintained at 75° C. throughout the addition by reducing the pressure from 210 to 90 mm Hg. Removal of xylene and volatile by-product distillates (55.0 g) was carried out during the addition. On completion of the paraformaldehyde addition, heating was continued at 75° C. under reduced pressure (90 mm Hg) for 1 hour to ensure completion of reaction and the mixture was then cooled to 30°–400° C.

The reaction mixture was drowned out into a mixture of water (500 g) and sulphuric acid (125.0 g), maintaining the temperature of the mixture between 40° and 50° C. The whole mixture was stirred at 40°–50° C. for 2 hours then allowed to settle and the upper (organic) layer was separated from the lower (aqueous) layer.

The organic layer was washed with hot water (2×250 g) until acid-free and xylene was then removed by distillation under reduced pressure to leave crude 5-nonylsalicylaldehyde as a yellow oil (126.25 g at 79.4% strength giving a yield of 80.0% from nonylphenol). The aldehyde was purified by distillation at 205°–210° C./20 mm Hg.

When the same reaction is performed in xylene at atmospheric pressure and a temperature of 105°–110° C., 129.1 g of crude 5-nonylsalicylaldehyde of 72.8% strength are obtained, giving a yield of 75.8% from nonylphenol.

I claim:

1. A method for the preparation of a 2-hydroxyarylaldehyde which comprises reacting a magnesium bis-hydrocarbyloxide, derived at least in part from a hydroxyaromatic compound having at least one free position ortho to the hydroxyl group, with formaldehyde or a formaldehyde-liberating compound under substantially anhydrous conditions at a pressure of from 50 to 700 mm Hg absolute.

2. A method according to claim 1 which comprises reacting the magnesium bis-hydrocarbyloxide with the formaldehyde or formaldehyde-liberating compound in the presence of a substantially anhydrous solvent system comprising an inert non-polar or low polarity organic solvent and a polar organic solvent.

3. A method according to claim 2 wherein the inert organic solvent comprises an aromatic hydrocarbon or a chlorinated aromatic hydrocarbon.

4. A method according to claim 3 wherein the aromatic hydrocarbon comprises toluene or xylene.

5. A method according to any one of claims 2 to 4 wherein the polar organic solvent comprises a polar aprotic solvent or a lower alkanol.

6. A method according to claim 5 wherein the lower alkanol comprises methanol.

7. A method according to claim 1 wherein the magnesium bis-hydrocarbyloxide is a magnesium bis-phenoxide wherein the phenoxide residues may be unsubstituted or may be substituted in any or all of the positions, other than both the 2- and 6- positions, by substituents which do not interfere with the course of the reaction.

8. A method according to claim 7 wherein the magnesium bis-phenoxide is derived from a phenol of the formula:

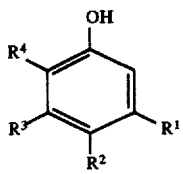 (1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy or acyl group.

9. A method according to claim 8 wherein each of the alkyl, cycloalkyl, aralkyl, aryl, alkaryl, alkoxy, aryloxy or acyl groups which may be represented by $R^1$, $R^2$, $R^3$ and $R^4$ contains from 5 to 22 carbon atoms.

10. A method according to claim 8 wherein the magnesium bis-phenoxide is derived from a phenol of the formula:

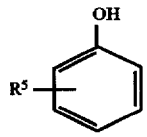 (3)

wherein $R^5$ represents hydrogen or a $C_{1-22}$-alkyl radical.

11. A method according to claim 10 wherein $R^5$ is a $C_7$-$_{12}$-alkyl radical.

12. A method according to claims 1, 2, 3, 4 or 7 wherein the magnesium bis-hydrocarbyloxide is the product of reacting a magnesium alkoxide of the formula:

$$Mg(OR^6)_2 \qquad (7)$$

wherein $R^6$ represents an alkyl radical with up to two moles of a phenol having at least one unsubstituted position ortho to the hydroxyl group.

13. A method according to claim 12 wherein the magnesium bis-hydrocarbyloxide is the product of reacting the magnesium alkoxide with from 0.9 to 2 moles of phenol per mole of magnesium alkoxide.

14. A method according to claim 13 wherein the magnesium bis-hydrocarbyloxide is the product of reacting the magnesium alkoxide with from 1.5 to 2 moles of phenol per mole of magnesium alkoxide.

15. A method according to claim 12 wherein $R^6$ is a $C_{1-4}$-alkyl radical.

16. A method according to claim 15 wherein the magnesium alkoxide is magnesium methoxide.

17. A method according to claim 1, 2, 3, 4 or 7 wherein the formaldehyde-liberating compound is paraformaldehyde.

18. A method according to claim 1, 2, 3, 4 or 7 wherein the amount of formaldehyde or formaldehyde-liberating compound used is at least 2 moles HCHO per mole of phenol present in the magnesium bis-hydrocarbyloxide.

19. A method according to claim 18 wherein the molar ratio of formaldehyde to phenol in the bis-hydrocarbyloxide is from 2 to 3.

20. A method according to claim 2, 3, 4 or 7 wherein the polar solvent is used in an amount not exceeding 5 moles per mole of magnesium bis-hydrocarbyloxide.

21. A method according to claim 20 wherein the polar solvent is used in an amount of from 1 to 2 moles per mole of bis-hydrocarbyloxide.

22. A method according to claim 1, 2, 3, 4 or 7 wherein the magnesium bis-hydrocarbyloxide is reacted with the formaldehyde or formaldehyde-liberating compound at a pressure of from 50 to about 500 mm Hg.

23. A method according to claim 1, 2, 3, 4 or 7 wherein the magnesium bis-hydrocarbyloxide is magnesium bis-(4-nonylphenoxide).

24. A method according to claim 23 which comprises reacting magnesium bis-(4-nonylphenoxide) with formaldehyde or a formaldehyde-liberating compound in the presence of a substantially anhydrous solvent system comprising toluene or xylene and methanol at a pressure of from 50 to about 400 mm Hg.

* * * * *